United States Patent [19]

Yoshida et al.

[11] Patent Number: 4,876,281

[45] Date of Patent: Oct. 24, 1989

[54] ANTIFUNGAL AGENTS

[75] Inventors: Susumu Yoshida; Shizutoshi Nakagawa; Tsuyoshi Ushiroguchi; Hiromichi Matsuura; Akira Yazaki, all of Koda, Japan

[73] Assignee: Wakunaga Seiyaku Kabushiki Kaisha, Osaka, Japan

[21] Appl. No.: 93,001

[22] Filed: Sep. 4, 1987

[30] Foreign Application Priority Data

Sep. 5, 1986 [JP] Japan ................... 61-208902

[51] Int. Cl.$^4$ ............................................. A61K 31/60
[52] U.S. Cl. ..................................... 514/517; 514/518; 514/707
[58] Field of Search ................... 514/517, 518, 707

[56] References Cited

U.S. PATENT DOCUMENTS 4,643,994  2/1987  Block et al. .................... 514/517

OTHER PUBLICATIONS

The Lancet, 1 (8212), 150-151 (1981).
Phytochemistry, 24, 1593-1594 (1985).
Folk Medicine: The Art and the Science, Chapt. 8, 125-137 (1986).
J. Am. Chem. Soc., 108, 7045-7055 (1986).

*Primary Examiner*—Jacqueline V. Howard

*Attorney, Agent, or Firm*—Wenderoth, Lind & Ponack

[57] ABSTRACT

An antifungal agent comprising as an effective component a polysulfide compound represented by formula $$R_1-S(O)_p-R_2 \qquad (A)$$

wherein
$R_1$ is $CH_3-$, $CH_2=CHCH_2-$ or $C_2H_5OCO(CH_2)_3-$,
p is an integer 1 or 2, and
$R_2$ is $-S-CH_2CH=CH_2$ or $-CH_2CH(H)\cdots CH(H)-S_q-S(O)_r-R_3$
in which
$-CH_2CH(H)\cdots CH(H)-$ is $-CH_2CH_2CH_2-$ or $-CH_2CH=CH-$,
q is an integer 0 or 1, r is integer from 0 to 2, and $R_3$ is selected from the group consisting of alkyl having 1 to 6 carbon atoms, benzyl, $-CH_2CH=CH_2$, $-CH_2CH=CHCH_3$, $-(CH_2)_3COOC_2H_5$, and $-CH=CHCH_2-S-(CH_2)_3COOC_2H_5$, with the proviso that p is 2 when $R_1$ is $CH_2=CHCH_2-$, $R_2$ is $-CH_2CH(H)\cdots CH(-H)-S_q-S(O)_r-R_3$, $-CH_2CH(H)\cdots CH(H)-$ is $-CH_2CH=CH-$, q is 1, r is 0 and $R_3$ is $-CH_2CH=CH_2$.

8 Claims, No Drawings

ANTIFUNGAL AGENTS

BACKGROUND OF THE INVENTION

1. Field of the Invention

This invention relates to antifungal agents comprising a specified sulfur-containing compound as an effective component, and in particular to novel use of the compound.

2. Description of the Prior Art

So far many drugs have been used for treating fungal infectious disease. They, however, present difficulties in causing side effects in both internal and external satisfactory drugs.

Attempts to extract medicinal substances or substances effective for treating the human body from natural materials have been made for a long time, and as well-known, a number of active substances obtained are supplied as drugs.

An example of garlic generally known as invigorant and tonic will be described: it has been used as stomachic, diaphoretic, diuretic, expectorant, intestinal medicine, germicide, vermicide, etc. In recent years it has become clarified that an efficacy of garlic, the platelet aggregation inhibitory activity, was attributable to the activity of methylallyltrisulfide found in the volatile constituent of garlic, the so-called garlic oil [Lancet, 1 (8212), 150–151 (1981)]. Also allicine in garlic was reported to have similar activity [Phytochemistry, 24, 1593–1594 (1985)]. Block, et al. reported a sulfur-containing compound isolated by them from garlic, ajoene, having the structural formula represented as

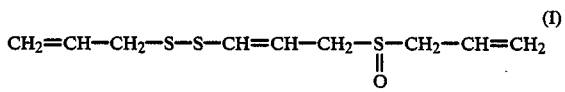
(I)

and demonstrated to have platelet aggregation inhibitory activity.

Another paper [Folk Medicine: The Art and the Science, Chapter 8: 125–137 (1986), American Chemical Society] reported that there were a number of compounds analogous to ajoene having the same activities, which are compounds 1 to 16 according to the invention listed later.

On the other hand, under concentrated effort on the study of ajoene, some of the present inventors have found ajoene has antifungal activity. [See Japanese Patent Publication No. 263121/1987.] Until now there ave been no reports describing such activity of sulfur-containing unsaturated aliphatic derivatives other than ajoene.

SUMMARY OF THE INVENTION

The invention is based on the discovery of the fact that specified sulfur-containing compounds have potent antifungal activities.

Thus, the antifungal agent in accordance with the invention comprises as an effective constituent a polysulfide compound represented by formula $$R_1—S(O)_p—R_2 \quad (A)$$

wherein
$R_1$ is $CH_3—$, $CH_2=CHCH_2—$ or $C_2H_5OCO(CH_2)_3—$,
p is an integer 1 or 2, and
$R_2$ is $—S—CH_2CH=CH_2$ or $—CH_2CH(H)\ CH(H)—S_q—S(O)_r—R_3$
in which
$—CH_2CH(H)\ CH(H)—$ is $—CH_2CH_2CH_2—$ or $—CH_2CH=CH—$, q is an integer 0 or 1, r is integer from 0 to 2, $R_3$ is selected from the group consisting of an alkyl having 1 to 6 carbon atoms, benzyl, $—CH_2CH=CH_2$, $—CH_2CH=CHCH_3$, $—(CH_2)_3COOC_2H_5$, and $—CH=CHCH_2—S—(CH_2)_3COOC_2H_5$,
with the proviso that p is 2 when $R_1$ is $CH_2=CHCH_2—$, $R_2$ is $—CH_2CH(H)\ CH(H)—S_q—S(O)_r—R_3$ in which $—CH_2CH(H)\ CH(H)—$ is $—CH_2CH=CH—$, q is 1, r is 0 and $R_3$ is $—CH_2CH=CH_2$.

The invention provides novel uses of known substances. Besides, as described later, antifungal agents according to the invention have only slight toxicity, and thus are expected to contribute much in the field of treatment of fungal infectious diseases where effective drugs are few in number.

DETAILED DESCRIPTION OF THE INVENTION

Antifungal agents according to the invention have a specified polysulfide compound as an effective constituent.

Polysulfide compounds

Suitable polysulfide compounds for use in the invention are represented by the above-mentioned formula (A).

These compounds are sulfonyl or sulfinyl compounds, as immediately understood from formula (A), and also can be stated to be polysulfide compounds in which the $R_2$ radical likewise has sulfur atoms in the form of thioether and/or sulfonyl or sulfinyl radical.

Examples of such compounds are shown in the Table given below. Of these compounds, ones having double bonds in the molecule at a site other than the terminals, for example, compounds 1, 3, 5 through 17 can exist as E and Z geometrical isomers, both of which are within the scope of the invention. All of these compounds except compound 17 have been synthesized for the first time by Block, et el., as stated above [Folk Medicine; The art and the Science, Chapter 8; 125–137 (1986), American Chemical Society, and J. Am. Chem. Soc. 108, 7045 (1986)].

| Compound No. | Structure |
|---|---|
| 1 | $CH_2=CHCH_2SCH_2CH=CHSSCH_2CH=CH_2$<br>$O_2$ |
| 2 | $CH_2=CHCH_2SCH_2CH_2CH_2SSCH_2CH=CH_2$<br>$O_2$ |

-continued

| Compound No. | Structure |
|---|---|
| 3 | $CH_2=CHCH_2SCH_2CH=CHSCH_2CH=CH_2$<br>$\quad\quad\quad\quad\quad O_2$ |
| 4 | $CH_2=CHCH_2SSCH_2CH=CH_2$<br>$\quad\quad\quad O_2$ |
| 5 | $CH_3SCH_2CH=CHSSCH_2CH=CH_2$<br>$\quad O$ |
| 6 | $CH_3SCH_2CH=CHSSCH_3$<br>$\quad O$ |
| 7 | $CH_2=CHCH_2SCH_2CH=CHSSCH_2CH=CH_2$<br>$\quad\quad\quad\quad O_2 \quad\quad\quad O$ |
| 8 | $CH_2=CHCH_2SCH_2CH=CHSSCH_2CH=CH_2$<br>$\quad\quad\quad\quad O_2 \quad\quad\quad O_2$ |
| 9 | $C_2H_5OOCCH_2CH_2CH_2SCH_2CH=CHSSCH_2CH=CH_2$<br>$\quad\quad\quad\quad\quad\quad\quad\quad O$ |
| 10 | $C_2H_5OOCCH_2CH_2CH_2SCH_2CH=CHSSCH_2CH_2CH_2COOC_2H_5$<br>$\quad\quad\quad\quad\quad\quad\quad\quad O$ |
| 11 | $C_2H_5OOCCH_2CH_2CH_2SCH_2CH=CHSSCH=CHCH_2SCH_2CH_2CH_2COOC_2H_5$<br>$\quad\quad\quad\quad\quad\quad\quad\quad O$ |
| 12 | $CH_2=CHCH_2SCH_2CH=CHSSCH_2CH_2CH_3$<br>$\quad\quad\quad\quad O_2$ |
| 13 | $CH_2=CHCH_2SCH_2CH=CHSSCH_2CH_2CH_2CH_2CH_2CH_3$<br>$\quad\quad\quad\quad O_2$ |
| 14 | $CH_2=CHCH_2SCH_2CH=CHSSCH_2CH=CHCH_3$<br>$\quad\quad\quad\quad O_2$ |
| 15 | $CH_2=CHCH_2SCH_2CH=CHSSCH_2CH=CHCH_2CH_3$<br>$\quad\quad\quad\quad O_2$ |
| 16 | $CH_2=CHCH_2SCH_2CH=CHSSCH_2-\!\!\!\!\bigcirc$<br>$\quad\quad\quad\quad O_2$ |
| 17 | $CH_2=CHCH_2SCH_2CH=CHSSCH_3$<br>$\quad\quad\quad\quad O$ |

Antifungal agents

Antifugal agents according to the invention comprise as an effective constituent a sulfur-containing unsaturated aliphatic derivative represented by the aforesaid formula (A). Compound 1 is most preferable because of its antifungal activity.

Such antifugal agents can be used for treating mammals including humans, particularly local fungal infectious diseases due to Candida, Trichophyton, Microsporum or Epidermophyton, and mucosal infectious diseases due to *Candida albicans*. The agents can be applied for treatment of, for example, systemic infectious diseases due to *Candida albicans, Cryptococcus neoformans, Aspergillus flavus, Aspergillus fumigatus, Coccidioides, Paracoccidioides, Histoplasma* or *Blastmyces*. Antifungal agents according to the invention can be effectively used not only in treatment for fungal infectious diseases in animals including humans and lower animals but also for fungal diseases in plants.

The antifungal agents comprise any compound represented by the formula (A) alone or in admixture, or in combination with one or more liquid or solid mediums such as vehicle, adhesive and diluent, and prepared in various forms of preparation as powder, granule, capsule, injection, ointment, aerosol, solution, etc. They can be administered orally or parenterally, and in combination with other drugs as desired. Dosages which are varied in accordance with age, weight and symptoms, are usually within the range of approximately 10 mg to 10 g/day, preferably 50 mg to 5 g/day for and adult per os or intravenously. The dosage per day may be divided into single dose or a plurality of doses.

They can be used as any of a parenteral preparation, ointment, eye ointment, vaginal suppository and tablet, emulsion, cream, etc.

Of these for external use, particularly ointment including eye ointment and suppository including vaginal suppository can be prepared in combination with any base medium, either oily or emulsive, in which hydrophobic drugs are soluble or dispersible. Suitable contents of compounds represented by formula (A) are within the range of 1 to 1000 μg/ml, preferably 20 to 200 μg/ml.

The compounds of formula (A) are believed to be of low toxicity since no mortality was observed after one week test where compound 1, one of the compounds of formula (A), was intraperitoneally administered to 5 male ICR mice of 5 weeks age.

DESCRIPTION OF THE PREFERRED EMBODIMENTS

Example 1

(Synthesis of Compounds)

Compounds used in accordance with the invention are known and, with the exception of Compound 17, were synthesized for the first time by Block, et al. as stated above. A new route to obtain Compounds 1 and 17 is described.

(a) Synthesis of Compound 1

Diallyldisulfide (3 g) was dissolved in a glacial acetic acid (20 ml) and supplied with 31% hydrogen peroxide solution (2 g). After 4 hours' standing at room temperature there were added to the mixture ethanol (150 ml) The resulting solution was adjusted to apparent pH of 5 with $Na_2CO_3$ and heated at 70° C. in a water bath for 2 hours. After having been allowed to cool, the product was washed twice with n-hexane (150 ml), and extracted twice with dichloromethane (150 ml). The dichloromethane layer was washed with 5% $NaHCO_3$ aqueous solution until the product became neutral and dried over anhydrous $MgSO_4$, and the solvent was distilled away. The resultant residue was subjected to silica gel chromatography to separate and purify a compound of a mixture of E:Z=5:1 (Yield: 10.34 g). This compound was demonstrated to have the structure specified by $^{13}C$-NMR($CDCl_3$·TMS) spectra as listed below.

Z isomer: 139.5, 132.5, 125.1, 124.5, 119.4, 116.9, 57.0, 51.9, 42.2,

E isomer: 136.4, 132.4, 125.0, 124.8, 119.3, 114.9, 56.5, 54.8, 41.4.

(b) Synthesis of Compound 17

Frozen garlic (about 6 kg) was processed according to the ordinary procedure (for details, see for example Japanese patent application No. 268177/1985), and the obtained oily fraction was subjected to silica gel chromatography (silica gel 300 g, eluent of ethyl acetate:acetone=20:1) to obtain ajoene (1.4 g) and oily Compound 17 (118 mg) having:

NMR (270 MHz, $C_5D_5N$)δ(ppm): 6.62 (d, 1H), 6.18 (m, 1H), 5.98 (m, 1H), 5.30–5.43 (m, 2H), 3.47–3.81 (m, 4H), 2.32 (s, 3H), MS (direct CI, isobutane, 70 eV): m/e 209 (M+1), 161 (M−47), 119 (M-89).

Example 2

(Pharmacological tests)

Strains for use in test: *Candida albicans*, IFO 1594 *Aspergillus niger*, IFO 9455

Culture medium: Liquid Sabouraud's medium (maltose 40 g, proteose peptone 10 g, distilled water 1000 ml)

Positive control: amphotericin B (Sigma) 5-fluorocytosine (Wako Junyaku, Japan)

Procedure:

(a) *Candida albicans*

A culture resulting from shaken cultivation at 37° C. overnight was diluted 100-fold with the culture medium and used as seed culture.

A sample was diluted with the culture medium to vary concentrations and poured into test tubes each to contain 5 ml, and the seed culture (100 μl) was inoculated. After cultivation with shaking at 37° C. for 18 hours, formalin (0.5 ml) was added, thoroughly mixed, and diluted 10-fold with the culture medium. The resultant liquor was measured for absorbancy at 660 nm. The growth rate (%) was determined according to the equation Growth rate (%) =

$$\frac{\text{Absorbancy of a sample-added culture}}{\text{Absorbancy of a sample-free control}} \times 100$$

(b) *Aspergillus niger*

A sample was diluted with culture medium to vary concentrations and poured into test tubes each to contain 5 ml, and a platinum loop of spores was inoculated in each tube. After shaken cultivation at 37° C. for 3 days, formalin (0.5 ml) was added and well mixed. The mixture was centrifuged at 3500 rpm for 10 minutes to collect fungi, which were in turn dewatered on a filter paper, dried at 100° C. for one hour and weighed. The growth rate was determined by the following equation Growth rate (%) =

$$\frac{\text{Dry weight of fungi from sample-added culture}}{\text{Dry weight of fungi from sample-free control}} \times 100$$

95% growth-inhibitory concentration (up to 5% growth rate): a mean value of sample concentrations producing 95% growth inhibitory effects.

| Sample | Results: 95% Growth inhibitory concentration (μg/ml) | |
|---|---|---|
| | *Candida albicans* | *Aspergillus niger* |
| Amphotericin B | 0.2 | >0.8 |
| 5-fluorocytosine | 20 | 80 |
| Compound 1 | 5.4 | 28.5 |
| Compound 5 | | 57.3 |
| Compound 7 | | 30.8 |
| Compound 10 | | 80.4 |
| Compound 16 | | 42.2 |
| Compound 17 | 40.7 | 49.1 |

Example 3

Compositions of preparations

| a. | Composition of injection | |
|---|---|---|
| | Compound 1 | 2,000 mg |
| | Tween 80 | 1,200 mg |
| | Sodium chloride | 4,300 mg |
| | Potassium chloride | 150 mg |
| | Calcium chloride | 165 mg |
| | Distilled water (for injection) | to make 500 ml |
| b. | Composition of granule | |
| | Compound 1 | 2,000 mg |
| | Silicic acid anhydride | 1,000 mg |
| | Lactose | A suitable amount |

| | | |
|---|---|---:|
| | Corn starch | 500 mg |
| | Croscarmellose sodium | 337.5 mg |
| | Total | 4,500 mg |
| c. | Composition of capsule | |
| | Compound 1 | 2,000 mg |
| | Panaceat | 310 mg |
| | Safflower oil | 510 mg |
| | Total | 2,820 mg |
| d. | Composition of ointment | |
| | Compound 1 | 20 g |
| | Stearic alcohol | 25 g |
| | Stearic acid | 5 g |
| | Macrogol | 5 g |
| | 1,2,6-hexanetriol | 5 g |
| | Propylene glycol | 40 g |
| | Total | 100 g |

What is claimed is:

1. An antifungal agent comprising as an effective component a polysulfide compound represented by the formula $$R_1-S(O)_p-R_2 \quad (A)$$

wherein
$R_1$ is $CH_3-$, $CH_2=CHCH_2-$ or $C_2H_5OCO(CH_2)_3-$,
p is an integer 1 or 2, and
$R_2$ is $-S-CH_2CH=CH_2$ or $-CH_2CH(H)CH(H)-S_q-S(O)_r-R_3$
in which
$-CH_2CH(H)CH(H)-$ is $-CH_2CH_2CH_2-$ or $-CH_2CH=CH-$,
q is an integer 0 or 1, r is integer from 0 to 2, and
$R_3$ is selected from the group consisting of alkyl having 1 to 6 carbon atoms, benzyl, $-CH_2CH=CH_2$, $-CH_2CH=CHCH_3$, $-(CH_2)_3COOC_2H_5$, and $-CH=CHCH_2-S-(CH_2)_3COOC_2H_5$, with the proviso that p is 2 when $R_1$ is $CH_2=CHCH_2-$, $R_2$ is $-CH_2CH(H)CH(H)-S_q-S(O)_r-R_3$ in which $-CH_2CH(H)CH(H)-$ is $-CH_2CH=CH-$, q is 1, r is 0 and $R_3$ is $-CH_2CH=CH_2$, and a carrier therefor, the antifungal agent being for combating pathogenic fungus selected from the group consisting of Candida and Aspergillus.

2. The antifungal agent as claimed in claim 1 wherein the polysulfide compound is selected from those set forth in the following list:

| Compound No. | Structure |
|---|---|
| 1 | $CH_2=CHCH_2SCH_2CH=CHSSCH_2CH=CH_2$<br>$O_2$ |
| 2 | $CH_2=CHCH_2SCH_2CH_2CH_2SSCH_2CH=CH_2$<br>$O_2$ |
| 3 | $CH_2=CHCH_2SCH_2CH=CHSCH_2CH=CH_2$<br>$O_2$ |
| 4 | $CH_2=CHCH_2SSCH_2CH=CH_2$<br>$O_2$ |

3. The antifungal agent as claimed in claim 2 wherein the polysulfide compound is Compound 1 set forth in the list.

4. A method of treating a fungal infectious disease which comprises administering to an object which is infected with pathogenic fungus selected from the group consisting of Candida and Aspergillus a pharmaceutically effective amount of a polysulfide compound represented by the formula $$R_1-S(O)_p-R_2 \quad (A)$$

wherein
$R_1$ is $CH_3-$, $CH_2=CHCH_2-$ or $C_2H_5OCO(CH_2)_3-$,
p is an integer 1 or 2, and
$R_2$ is $-S-CH_2CH=CH_2$ or $-CH_2CH(H)CH(H)-S_q-S(O)_r-R_3$
in which
$-CH_2CH(H)CH(H)-$ is $-CH_2CH_2CH_2-$ or $-CH_2CH=CH-$,
q is an integer 0 or 1, r is integer from 0 to 2, and
$R_3$ is selected from the group consisting of alkyl having 1 to 6 carbon atoms, benzyl, $-CH_2CH=CH_2$, $-CH_2CH=CHCH_3$, $-(CH_2)_3COOC_2H_5$, and $-CH=CHCH_2-S-(CH_2)_3COOC_2H_5$, with the proviso that p is 2 when $R_1$ is $CH_2=CHCH_2-$, $R_2$ is $-CH_2CH(H)CH(H)-S_q-S(O)_r-R_3$ in which $-CH_2CH(H)CH(H)-$ is $-CH_2CH=CH-$, q is 1, r is 0 and $R_3$ is $-CH_2CH=CH_2$.

5. The method as claimed in claim 4 wherein the polysulfide compound is selected from those set forth in the following list:

| Compound No. | Structure |
|---|---|
| 1 | $CH_2=CHCH_2SCH_2CH=CHSSCH_2CH=CH_2$<br>$O_2$ |
| 2 | $CH_2=CHCH_2SCH_2CH_2CH_2SSCH_2CH=CH_2$<br>$O_2$ |
| 3 | $CH_2=CHCH_2SCH_2CH=CHSCH_2CH=CH_2$<br>$O_2$ |
| 4 | $CH_2=CHCH_2SSCH_2CH=CH_2$<br>$O_2$ |

-continued

| Compound No. | Structure |
|---|---|
| 5 | $CH_3SCH_2CH=CHSSCH_2CH=CH_2$<br>    $O$ |
| 6 | $CH_3SCH_2CH=CHSSCH_3$<br>    $O$ |
| 7 | $CH_2=CHCH_2SCH_2CH=CHSSCH_2CH=CH_2$<br>           $O_2$            $O$ |
| 8 | $CH_2=CHCH_2SCH_2CH=CHSSCH_2CH=CH_2$<br>           $O_2$            $O_2$ |
| 9 | $C_2H_5OOCCH_2CH_2CH_2SCH_2CH=CHSSCH_2CH=CH_2$<br>                        $O$ |
| 10 | $C_2H_5OOCCH_2CH_2CH_2SCH_2CH=CHSSCH_2CH_2CH_2COOC_2H_5$<br>                        $O$ |
| 11 | $C_2H_5OOCCH_2CH_2CH_2SCH_2CH=CHSSCH=CHCH_2SCH_2CH_2CH_2COOC_2H_5$<br>                        $O$ |
| 12 | $CH_2=CHCH_2SCH_2CH=CHSSCH_2CH_2CH_3$<br>           $O_2$ |
| 13 | $CH_2=CHCH_2SCH_2CH=CHSSCH_2CH_2CH_2CH_2CH_2CH_3$<br>           $O_2$ |
| 14 | $CH_2=CHCH_2SCH_2CH=CHSSCH_2CH=CHCH_3$<br>           $O_2$ |
| 15 | $CH_2=CHCH_2SCH_2CH=CHSSCH_2CH=CHCH_2CH_2CH_3$<br>           $O_2$ |
| 16 | 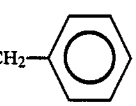 |
| 17 | $CH_2=CHCH_2SCH_2CH=CHSSCH_3$<br>           $O_2$ |

6. The method as claimed in claim 5 wherein the polysulfide compound is Compound 1 set forth in the list.

7. The method as claimed in claim 4 wherein the object is an animal.

8. The method as claimed in claim 4 wherein the animal is a human.

* * * * *